LIQUID FORMULATIONS OF 1-(3,4-DICHLOROPHENYL)-3-METHOXY-3-METHYLUREA AND SELECTED CHLOROACETAMIDES

CROSS-REFERENCE TO RELATED APPLICATIONS

This application is a continuation-in-part of my copending application Ser. No. 665,328, filed Mar. 9, 1976, now abandoned which in turn is a continuation-in-part of Ser. No. 581,952, filed May 29, 1975, now abandoned which is a continuation of Ser. No. 320,479, filed Jan. 2, 1973, now abandoned, which is a continuation-in-part of Ser. No. 33,912, filed May 1, 1970, now abandoned, which is a continuation-in-part of Ser. No. 814,167, filed Apr. 7, 1969, now abandoned, which is a continuation-in-part of Ser. No. 781,597, filed Dec. 5, 1968, now abandoned, which is a continuation-in-part of application Ser. No. 732,018, filed May 27, 1968, now abandoned.

BACKGROUND OF THE INVENTION

This invention relates to novel liquid agricultural solution concentrates which, because of solution synergism, have improved properties, e.g., lower crystallization temperatures. These concentrates are useful as herbicides. The active component in the concentrates is a mixture of 1-(3,4-dichlorophenyl)-3-methoxy-3-methylurea, hereinafter called linuron, and 2-chloro-N-isopropylacetanilide, hereinafter called propachlor, or 2-chloro-2',6'-diethyl-N-(methoxymethyl)-acetanilide, hereinafter called alachlor.

The invention further relates to the method of preparing solution concentrates of linuron by combining linuron with a chloroacetanilide selected from the group consisting of propachlor and alachlor in a suitable organic solvent.

Linuron, propachlor and alachlor are herbicides that have been found wide application in weed control programs. It is also known that combinations of linuron and propachlor, as well as linuron and alachlor, exhibit outstanding weed control in corn, sorghum and soybeans both in pre-emergence and post-emergence applications.

Linuron and propachlor have been prepared for use either as granules or as wettable powders. Because of the irritating and toxic nature of propachlor, the dustiness of dry formulations such as wettable powders represents not only an irritation, but also an actual hazard to persons carelessly handling these formulations. This hazard is of particular importance in the manufacture of wettable powders in which the requirement of dust-tight equipment increases the cost and difficulty of producing the formulation. The properties of linuron are such that a solution concentrate is difficult to produce.

Agricultural weed killers, like many other formulated products, must meet a variety of exacting requirements before they are commercially useful. In the case of liquid formulations, they must be stable in storage both at high and low temperatures. Concentrates for application in water must emulsify well when diluted at many different concentrations with water of different types and hardness.

It is known that solution concentrates of linuron, at economically practical concentrations, are not stable when in cold temperature storage. Linuron crystals will form in the concentrates upon storage at moderately low or even room temperatures. When crystallization occurs in large containers as, for example, in a 30-gallon drum in a warehouse, such crystals form dense, thick layers at the bottom of the drum. It is usually impractical or at least very difficult to re-establish a homogeneous solution even when the contents of the drum are warmed. It was, therefore, believed that dry formulations such as wettable powders and granules, were the most acceptable type for formulations containing linuron as an active ingredient.

SUMMARY OF THE INVENTION

It has now been discovered that linuron, when combined with propachlor or alachlor at a weight ratio of linuron to the chloroacetanilide of from 1:1 to 1:3, can be dissolved in a suitable solvent because of solution synergism at suitable liquid concentrate concentrations, and that these solutions are suitable for storage at lower temperatures than could be used for linuron in the absence of the chloroacetanilide. These solutions containing a mixture of linuron and either of the chloroacetanilides, as described in greater detail hereinafter, have better low-temperature storage characteristics than either individual active constituent thereof has in solution at the same concentration. The solubility of the linuron in particular is greatly enhanced.

The term "low-temperature" will be understood to refer to temperatures in the range of 0° to 5° C. and lower. For practical purposes, a formulation which is stable at a temperature of from 0° to 5° C. will be sufficiently stable to withstand temperatures encountered in normal commercial handling of agricultural chemicals.

By "solution synergism" it is meant that the solubility of linuron in the solvent is increased by mixing the linuron with alachlor or propachlor. In addition to reducing the amount of solvent needed to dissolve a given amount of linuron, the alachlor or propachlor serves as an active ingredient.

The practice of this invention also results in lower manufacturing costs as the solution concentrates hereof can be prepared by dissolving the herbicidal components and agricultural modifiers in simple equipment; moreover, dust contamination is not a hazard. In addition, the user of these concentrates finds it easy to measure and pour the same with minimum skin exposure and no risk of breathing the dusts inherent in the handling of wettable powders.

DETAILED DESCRIPTION OF THE INVENTION

This invention relates to novel solution concentrates containing linuron, a substituted chloroacetanilide selected from the group consisting of alachlor or propachlor, and a solvent, e.g. an aromatic hydrocarbon or a halocarbon. These concentrates will contain from 15-50% by weight of active ingredient. The active ingredient consists of a combination on of linuron and said substituted chloroacetanilide in which the linuron to chloroacetanilide weight ratio is from 1:1 to 1:3. The preferred concentration of the active ingredient is about 25-45% by weight of the total composition. The preferred solution concentrates hereof also include an emulsifying agent. In addition, they can include a cosolvent and an oil-soluble corrosion inhibitor. Such cosolvents can comprise up to 40% of the total solvent present in the formulation.

United States Patent [19]

Baker, Jr.

[11] 4,163,662

[45] Aug. 7, 1979

[54] LIQUID FORMULATIONS OF 1-(3,4-DICHLOROPHENYL)-3-METHOXY-3-METHYLUREA AND SELECTED CHLOROACETAMIDES

[75] Inventor: Harris M. Baker, Jr., Wilmington, Del.

[73] Assignee: E. I. Du Pont de Nemours and Company, Wilmington, Del.

[21] Appl. No.: 779,825

[22] Filed: Mar. 21, 1977

Related U.S. Application Data

[63] Continuation-in-part of Ser. No. 665,328, Mar. 9, 1976, abandoned, which is a continuation-in-part of Ser. No. 581,952, May 29, 1975, abandoned, which is a continuation of Ser. No. 320,479, Jan. 2, 1973, abandoned, which is a continuation-in-part of Ser. No. 33,912, May 1, 1970, abandoned, which is a continuation-in-part of Ser. No. 814,167, Apr. 7, 1969, abandoned, which is a continuation-in-part of Ser. No. 781,597, Dec. 5, 1968, abandoned, which is a continuation-in-part of Ser. No. 732,018, May 27, 1968, abandoned.

[51] Int. Cl.$^2$ .............................................. A01N 9/20
[52] U.S. Cl. ........................................ 71/120; 71/118; 71/DIG. 1
[58] Field of Search ........................... 71/118, DIG. 1

[56] References Cited

U.S. PATENT DOCUMENTS

| | | | |
|---|---|---|---|
| 2,863,752 | 12/1958 | Hamm et al. | 71/118 |
| 3,139,333 | 6/1964 | Scott | 71/118 |
| 3,169,850 | 2/1965 | Thompson | 71/118 |
| 3,436,208 | 4/1969 | Lemin | 71/118 |
| 3,547,620 | 12/1970 | Olin | 71/118 |

FOREIGN PATENT DOCUMENTS

1176547  1/1970  United Kingdom ..................... 71/118

OTHER PUBLICATIONS

Trevett et al., "Preemergence Weed Control, etc.," (1966), Proc. N.E.W.C.C., 20 pp. 648–655, (1966).
Mitchell et al., "Evaluation of Sorvral, etc.," (1969), CA 11, No. 29479q., (1969).
Ser. No. 496,175, Olin – Phytotoxicants, (Arnd.), (1965), pp. 9, 19, 21 & 22, (1965).

*Primary Examiner*—Glennon H. Hollrah

[57] ABSTRACT

Mixtures of 1-(3,4-dichlorophenyl)-3-methoxy-3-methylurea with 2-chloro-N-isopropylacetanilide or 2-chloro-2',6'-diethyl-N-(methoxymethyl)acetanilide exhibit surprisingly high solubility in suitable solvents. This solution synergism is believed to be the result of molecular complexing of 1-(3,4-dichlorophenyl)-3-methoxy-3-methylurea with 2-chloro-N-isopropylacetanilide or with 2-chloro-2',6'-diethyl-N-(methoxymethyl)acetanilide.

18 Claims, No Drawings

The temperature limits below which crystallization of solute will occur can be measured by storing samples in a controlled temperature chest, seeding with tiny crystals of pure materials and observing the growth or disappearance of crystals after a period of several days. If no crystals form, the process is then repeated at a lower temperature, until the limit of stability has been found. However, crystallization characteristics can be also meaningfully, rapidly and conveniently measured by a determination of the cloud point of the system.

Cloud point determination provides a means, in addition to crystallization temperature measurement, by which storage stability may be determined.

A cloud point is the equilibrium temperature at which solids first separate from a previously clear solution. For example, if a solution has a cloud point of 5° C., then a solution which is cooled to 5° would be expected to have the first solids and be in equilibrium with saturated solution. In practice, to avoid supercooling effects, cloud points are usually measured by cooling a solution further, to obtain a copious crop of crystals. The solution is slowly warmed and the temperature at which the crystals finally disappear is determined.

Preferred formulations of this invention will have a cloud point of 5° C. or lower, those formulations being most preferred which have a cloud point below 0° C. It will, of course, be understood that the stability requirements for a particular formulation will be contingent on the time of year the formulation is shipped, length of storage planned, and geographic destination of the formulation. Usually a cloud point of about 5° C. is acceptable although a formulation with a lower cloud point will be employed when the formulation is to be shipped or stored in cold climates during the winter season.

To further illustrate the low temperature stability of a formulation of this invention a cold storage test can be run. This test differs from the cloud point determination in that equilibrium conditions are attained in the cold storage system, while a dynamic aspect is present in a cloud point determination.

EXAMPLE 1

Purified linuron, purified propachlor, purified alachlor and commercial "Triclene" (trichloroethylene, technical) are used in the procedure. Samples containing various ratios and concentrations of linuron, propachlor, and linuron-propachlor mixtures are placed in a cold chest. The temperature is lowered and samples are seeded with traces of dust of the active ingredients after the solution has been cooled to the test temperature of −5° C. The samples are then observed over the course of at least 3 to 4 days to determine whether crystallization has occurred. When the temperature of the system is maintained within the range of −4.5° to −5.0° C. for 4 days after seeding. The maximum solution concentration in grams of active ingredient per 100 grams of solvent, at which no crystallization occurs (Max. Stable), and the minimum solution concentration at which crystals first appear (Min. Unstable) are observed.

TABLE I

| | Cold Storage Test at −5° C. | | | |
|---|---|---|---|---|
| | Concentration in grams/100 grams Solvent | | Max. Solubility Range | |
| Weight Ratio Propachlor:Linuron | Max. Stable | Min. Unstable | Linuron | Propachlor |
| 1:0 | 21.9 | 25 | | 21.9–25 |
| 0:1 | 4.1 | 5.2 | 4.1–5.2 | |
| 1:1 | 14.9 | 16.3 | 7.4–8.1 | 7.4–8.1 |
| 2:1 | 42.8 | 44.9 | 14.2–14.9 | 28.5–29.9 |
| 3:1 | 38.9 | — | >9.7 | >29.2 |

The above data show that at a 1:1 ratio of propachlor to linuron results in at least an 80% increase in linuron solubility based on the solvent as compared with a solution containing no propachlor; at the 2:1 ratio the increase in linuron solubility is 240% and at the 3:1 ratio the increase in linuron solubility is 135%. At the 2:1 and 3:1 propachlor-to-linuron ratios, the propachlor solubility also increases.

EXAMPLE 2

A similar test was run replacing propachlor with alachlor and at +3° C. and at −8° to −9° C. with the following results:

TABLE II

| | Cold Storage Test at 3° C. | | |
|---|---|---|---|
| | Concentration in grams/100 grams Solvent | | Max. Solubility Range For Linuron |
| Weight Ratio Alachlor:Linuron | Max. Stable | Min. Unstable | |
| 0:1 | 4.1 | 4.7 | 4.1–4.7 |
| 1:2 | 11.7 | 13.6 | 7.9–8.9 |
| 1:1 | 16.2 | 19.0 | 8.1–9.5 |
| 2:1 | 42.8 | — | >14.3 |
| 3:1 | 47.0 | — | >11.7 |
| (Cold Storage Test at −8° to −9° C.) | | | |
| 0:1 | 3.6 | 4.1 | 3.6–4.1 |
| 1:2 | 6.3 | 8.1 | 4.2–4.8 |
| 1:1 | 13.6 | 16.2 | 6.8–8.1 |
| 2:1 | 31.6 | 37.0 | 10.5–12.3 |
| 3:1 | 38.9 | 47.0 | 9.7–11.7 |

Here again the solubility of linuron more than doubled at the 2:1 molar ratio of substituted chloroacetanilide to linuron.

EXAMPLE 3

Samples weighing 5 grams each total weight were prepared by mixing the indicated solids and liquids, in the indicated proportions and shaking in closed vials, which were sealed with epoxy cement to prevent evaporation.

Tables III, IV, and V show the proportions of each mixture and the amounts of insoluble, crystalline material observed in each case after room temperature storage:

TABLE III

| weight % linuron | 9 | 17 | 17 | 17 | — |
|---|---|---|---|---|---|
| weight % propachlor | — | — | 34 | — | 34 |
| weight % alachlor | — | — | — | 34 | — |
| weight % xylene | 91 | 83 | 49 | 49 | 66 |
| crystalline material | slight | heavy | none | none | moderate |

TABLE IV

| weight % linuron | 5 | 9 | 9 | 9 | — |
|---|---|---|---|---|---|
| weight % propachlor | — | — | 18 | — | 18 |

TABLE IV-continued

| weight % alachlor | — | — | — | 18 | — |
|---|---|---|---|---|---|
| weight % tetrachloroethylene | 95 | 91 | 73 | 73 | 82 |
| crystalline material | moderate | heavy | none | none | moderate |

TABLE V

| weight % linuron | 10 | 15 | 15 | 15 | — |
|---|---|---|---|---|---|
| weight % propachlor | — | — | 30 | — | 30 |
| weight % alachlor | — | — | — | 30 | — |
| weight % "Panasol" AN-3 | 90 | 85 | 55 | 55 | 70 |
| crystalline material | moderate | heavy | none | none | moderate |

The above results, again, show the beneficial effect of alachlor and propachlor on the solubility of linuron in hydrocarbons and halocarbons. When linuron or the chloroacetanilide were shaken in the solvent alone, crystals remained. When the linuron and a chloroacetanilide were shaken together at the same concentrations in the same solvent, complete solutions were obtained, indicating better solubility.

It is believed that linuron on the one hand and alachlor or propachlor on the other hand form molecular complexes which have considerably higher solubility in hydrocarbons and in halocarbons than linuron alone. The amount of linuron which can thus be dissolved and will remain in the solution even at a low temperature is larger than the amount of linuron which can be dissolved in the same solvent at the same temperature in the absence of alachlor and propachlor. These molecular complexes probably are hydrogen bonded.

One can find support for this theory by examining the nuclear magnetic resonance (N.M.R.) spectra of linuron, alachlor, propachlor, and mixtures of linuron with alachlor and linuron with propachlor. The method of determination of the N.M.R. spectra of these compounds as well as the N.M.R. data, are discussed in detail below:

Nuclear Magnetic Resonance Experiments

In the first series of experiments, A, NMR spectra of pure 1-(3,4-dichlorphenyl)-3-methoxy-3-methylurea (linuron), 2-chloro-2',6'-diethyl-N-(methoxymethyl)acetanilide (alachlor), 2-chloro-N-isopropylacetanilide (propachlor), and of equimolar quantities of linuron-alachlor and linuron-propachlor, all in deuterated chloroform, were taken. In each case, solutions containing 0.001 mole of each compound in 1 ml of $CDCl_3$ were prepared. The mixtures were prepared similarly by dissolving a mixture containing 0.001 mole of each component in 1 ml of $CDCl_3$. All spectra were taken using a Varian Associates Model T-60 nuclear magnetic resonance spectrometer with tetramethylsilane (TMS) as internal standard.

The above experiments were repeated, B, using linuron-alachlor and linuron-propachlor molar ratios of 1:3. In these experiments, the linuron concentration was one-third of that in experiments A.

The formulas of linuron, alachlor and propachlor are given below, and each type of proton is indicated by a figure in parentheses in the same order in which its signal appears in the spectrum starting with the signal appearing at the highest field (closest to the TMS signal) as number 1.

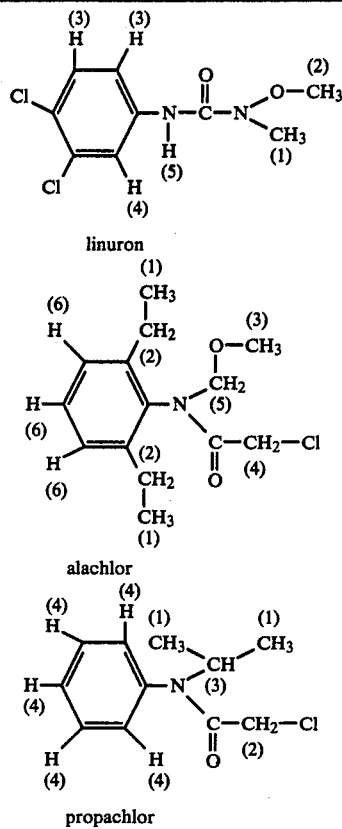

The results are presented in Tables VI and VII below.

TABLE VI

Position of NMR signals in Cycles per Second Downfield from TMS

| Proton No. | linuron | alachlor | Propachlor |
|---|---|---|---|
| 1 | 190S | 75T | 65D |
| 2 | 225S | 157Q | 224S |
| 3 | 440D | 210S | 300M |
| 4 | See Table VII | 223S | 440M |
| 5 | See Table VII | 300S | |
| 6 | | 437M | |

S = singlet,
D = doublet,
T = triplet,
Q = quartet,
M = multiplet

TABLE VII

Positions and Shifts of NMR Signals in Cycles Per Second Downfield from the TMS Signal

| Experiment | linuron Proton No. | linuron Alone | linuron + propachlor | Shift | linuron + alachlor | Shift |
|---|---|---|---|---|---|---|
| A | 4 | 465 | 470 | 5 | 469 | 4 |
|   | 5 | 473 | 488 | 15 | 485 | 12 |
| B | 4 | 462 | 464 | 2 | 464 | 2 |
|   | 5 | 465 | 478 | 13 | 476 | 11 |

Table VI shows the positions and types of the signals from protons 1-3 in linuron, 1-6 in alachlor and 1-4 in propachlor. The positions of those signals remained unchanged through experiments A and B.

Proton No. 4 in linuron (the aromatic proton in position 2) and No. 5 in linuron (the N-H proton), however, are shifted downfield in the mixtures, as seen in Table VII. These shifts are indicative of a hydrogen-bonding effect. The downfield shifts observed for linuron alone as well as for mixtures in going from the conditions of experiments A to B, are explained by a dilution effect, which is also indicative of hydrogen-bonding.

It can be concluded from the above results that the most reasonable explanation of the observed NMR shifts, combined with the unusual solubility properties of the mixtures of the present invention, is the formation of hydrogen-bonded complexes in which a hydrogen bond involves the —NH proton of linuron and the amide function of propachlor and alachlor, as the case may be. Molecular models show that in such complexes the bulk of the polar functions of the participation molecules would be located in the center of the volume which the complex occupies, while the less polar, and thus more soluble, portions of the molecule would be located on the surface of that volume. Therefore, drastically increased solubility, even in solvents of low polarity, should and does in fact result.

The compositions of this invention can be used to selectively control weeds in crops, particularly corn, sorghum and soybeans. The compositions can be applied at rates of 1 to six kilograms per hectare. The exact rate to be used will depend upon the crop, the soil type, the climate and the weeds to be controlled. The treatment will control both broadleaved weeds and grasses. The exact rate to be used can be readily selected by one skilled in the art from the available literature.

The following Examples are presented to further illustrate this invention. Parts and percentages in the following Examples are by weight.

EXAMPLE 4

An emulsifiable concentrate is prepared by stirring the ingredients listed below until solution is complete.

|  | SAMPLE A | SAMPLE B |
| --- | --- | --- |
| Linuron | 10% | 10% |
| Propachlor | 20% | 0% |
| Dodecylbenzenesulfonic acid | 19% | 19% |
| "Panasol" AN-3 | 51% | 71% |

The cloud point of Sample A is −25° C. The cloud point of Sample B is −15° C., thus illustrating the improved stability against crystal formation for the linuron/propachlor combination at the same linuron content and at a higher and more economical total active ingredient content and at a lower and more economical content of inert solvents.

Three kilograms of Sample A are emulsified in 300 l. of water and applied pre-emergence to one hectare of corn planted in a Clarion silt loam soil. The treatment controls giant foxtail (Setaria faberii), crabgrass, velvetleaf, goosegrass (Eleusine indica), barnyardgrass, prostrate spurge (Euphorbia supina), Pennsylvania smartweed (Polygonum pensylvanicum), and the corn grows and produces a good yield.

EXAMPLE 5

An emulsifiable concentrate is prepared by stirring the ingredients listed below until solution is complete.

|  | SAMPLE A | SAMPLE B |
| --- | --- | --- |
| Linuron | 7.5% | 7.5% |
| Propachlor | 7.5% | 0% |
| Nonylphenoxy polyethoxyethanol | 5.0% | 5.0% |
| "Espesol" No. 5 | 80.0% | 87.5% |

The cloud point of Sample A is +17° C. The cloud point of Sample B is +25° C.

Two kilograms of Sample A are emulsified in 200 l. of water and applied pre-emergence to a hectare of soybeans planted in a silt loam soil. The treatment provides control of crabgrass (Digitaria spp.), flower-of-an-hour(Hibiscus trionum), velvetleaf (Abutilon theophrasti), barnyardgrass (Echinochloa crusgalli), the foxtails (Setaria spp.), pigweed (Amaranthus retroflexus), and witchgrass (Panicum capillare). The soybeans grow and produce a good yield, free of weed competition.

EXAMPLE 6

An emulsifiable concentrate is prepared by stirring the ingredients listed below until solution is complete.

|  | SAMPLE A | SAMPLE B |
| --- | --- | --- |
| Linuron | 11.8% | 11.8% |
| Propachlor | 23.6% | 0% |
| Polyoxyethylene sorbitan oleate/polyoxyethylene amine blend | 3.7% | 3.7% |
| Monochlorobenzene | 30.5% | 42.25% |
| 1,1,2,2-tetrachloroethane | 30.4% | 42.24% |

The cloud point of Sample A is +8° C. The cloud point of Sample B is +15° C.

Two and one quarter kilograms of the active ingredients are emulsified in 300 liters of water and applied to one hectare of sorghum planted in a Sassafras sandy loam soil. The treatment is applied pre-emergence to both the crop and weeds. Some of the weeds controlled include velvetleaf (Abutilon theophrasti), goosegrass (Eleusine indica), jimson weed (Datura stramonium), curly duck (Rumex crispus).

EXAMPLE 7

A solution suitable for direct application is prepared by combining and stirring the following ingredients:

|  | SAMPLE A | SAMPLE B |
| --- | --- | --- |
| Linuron | 12.5% | 12.5% |
| Alachlor | 37.5% | 0% |
| Monochlorobenzene | 50.0% | 87.5% |

The cloud point of Sample A is −25° C. The cloud point of Sample B is −22° C.

If desired this material can be diluted with aromatic naphtha for application at somethat lower concentrations.

For liters of the above direct application concentrate are applied pre-emergence to a hectare of corn planted in a Flanigan silt loam. The application is made without dilution using an Econamizer ® application system. The treatment provides control of the weeds infesting the field including crabgrass (Digitaria spp.), velvetleaf (Abutilon theophrasti), goosegrass (Eleusine indica), green foxtail (*Setaria viridis*), and common ragweed (*Ambrosia artimiifolia*).

EXAMPLE 8

Emulsifiable concentrates are prepared by stirring the ingredients listed below until solution is completed.

|  | SAMPLE A | SAMPLE B |
|---|---|---|
| Linuron | 19.5% | 19.5% |
| Alachlor | 19.5% | 0% |
| Anionic/non-ionic blended emulsifier ("Atlox" 3459) | 5.0% | 5.0% |
| Methanol | 5.0% | 5.0% |
| Panasol AN-3 | 51.0% | 70.5% |

The cloud point of Sample A is +18° C. The cloud point of Sample B is +22° C., thus illustrating the improved stability against crystal formation for the linuron/alachlor combination at the same linuron content at a higher and more economical total active ingredient content and at a lower and more economical content of inert solvent.

Two kilograms active ingredient of Sample A are emulsified in 200 l. of water and applied preemergence to a hectare of soybeans planted in a silt loam soil. The treatment provides control of numerous weeds including pigweed (*Amaranthus retroflexus*), crabgrass (*Digitaria spp.*), lambsquarter (*Chemopodium album*), giant foxtail (*Setaria faberii*), and barnyardgrass (*Echinochloa crusgalli*).

In Examples 4 thru 8, the linuron-chloroacetamide mixture have lower cloud points than the corresponding sample without the chloroacetamide, but with additional solvent. This indicates that the linuron-chloroacetamide mixtures have lower freeze points and that the linuron is more soluble in the A samples.

EXAMPLE 9

| Ingredient | Sample A wt. % | Sample B wt. % |
|---|---|---|
| Linuron | 20 | 20 |
| Alachlor | 40 | — |
| "Sponto" N500B | 3 | 3 |
| "Sponto" N300B | 3 | 3 |
| Isophorone | 11.4 | 24.7 |
| Tenneco 500-100 oil | 22.6 | 49.3 |

Sample A was prepared by dissolving 5.0 gm of linuron, 10.0 gm of alachlor, 0.75 gm of "Sponto" N500B and 0.75 gm of "Sponto" N300B in a solvent composed of 2.85 gm isophorone and 5.65 gm Tenneco 500-100 oil.

Sample B was prepared by dissolving 5.0 gm of linuron, 0.75 gm "Sponto" N500B and 0.75 gm "Sponto" N300B a solvent composed of 6.18 gm isophorone and 12.32 gm of Tenneco 500-100 oil.

"Sponto" N500B and "Sponto" N300B are trade names for Witco Chemical Corporation liquid blends of anionic/nonionic, oil soluble sulfonates with polyoxyethylene ethers.

Tenneco 500-100 oil is a xylene-range aromatic solvent produced by Tenneco Oil Co.

Samples A and B were stored at −6° C. After they were equilibrated at −6° C., Sample A was seeded with a few crystals of linuron and alachlor and Sample B was seeded with linuron to initiate crystallization. After 6 days storage at −6° C., the liquids and solids were separated by filtration while cold. The liquid samples from A and B and the mixed solids from Sample A were assayed. The mixed solids from Sample A contained both linuron and alachlor indicating both were at liquid-solid equilibrium. The liquids contained the following:

| Sample | lb. linuron/lb. solvent | lb. alachlor/lb. solvent |
|---|---|---|
| Sample A liquids | 0.34 | 0.73 |
| Sample B liquids | 0.19 | — |

These results clearly show that linuron is much more soluble (more than 60% greater) in a 2:1 Tenneco 500-100 oil:isophorone solvent system when alachlor is present than when alachlor is not present.

EXAMPLE 10

| Ingredient | Sample A | | Sample B | |
|---|---|---|---|---|
|  | wt. % | wt. gm | wt. % | wt. gm |
| Linuron | 20 | 5.0 | 20 | 5.0 |
| Alachlor | 40 | 10.0 | — | — |
| Isophorone | 13.3 | 3.33 | 26.7 | 6.68 |
| Tenneco 500-100 | 26.7 | 6.67 | 53.3 | 13.32 |

Samples A and B of this example differ from those of Example 9 in that the former two samples were prepared without the "Sponto" surfactants. They were stored at −6° C., seeded and evaluated like those in the preceeding example. The mixed solids removed from Sample A contained both linuron and alachlor indicating both were at equilibrium with the liquid at −6° C. The liquids were analyzed and found to contain the following:

| Sample | lb. linuron/lb. solvent | lb. alachlor/lb. solvent |
|---|---|---|
| Sample A liquids | 0.30 | 0.74 |
| Sample B liquids | 0.16 | — |

Those results again clearly indicate that linuron is much more soluble (nearly 90% greater) in a 2:1 Tenneco 500-100 oil:isophorone solvent system where alachlor is present. In addition, this example shows that the "Sponto" surfactants in Example 9 were not responsible for the increased linuron solubility.

EXAMPLE 11

| Ingredient | Sample A | | | |
|---|---|---|---|---|
|  | wt. % | wt. gm | wt. % | wt. gm |
| Linuron | 19.5 | 3.9 | 19.5 | 3.9 |
| Alachlor | 19.5 | 3.9 | — | — |
| "Atlox" 3459 | 5.0 | 1.0 | 5.0 | 1.0 |
| Methanol | 5.0 | 1.0 | 5.0 | 1.0 |
| Panesol AN-3 | 51.0 | 10.2 | 70.5 | 14.1 |

These two solutions are a repeat of Example 8. However, the solutions were stored at −6° C., seeded with crystals of linuron and/or alachlor to initiate crystallization. After solid-liquid equilibrium at −6° C. was assured, the liquids were separated, while cold, from the solids by filtration. The solid from Sample A were analyzed and found to contain 99% linuron, indicating the linuron was at equilibrium in the solid and liquid. The liquids were analyzed and found to contain the following:

| Sample | lb. linuron/lb. solvent | lb. alachlor/lb. solvent |
|---|---|---|
| Sample A, liquid | 0.15 | 0.34 |
| Sample B, liquid | 0.087 | — |

These results again illustrate higher linuron solubility in a solvent system of this invention when alachlor is present than when alachlor is absent.

I claim:

1. A solution concentrate of an herbicidal formulation comprising from 15–50% by weight of a mixture of 1-(3,4-dichlorophenyl)-3-methoxy-3-methylurea and a chloroacetanilide selected from the group consisting of 2-chloro-N-isopropyl acetanilide and 2-chloro-2',-6'-diethyl-N-(methoxymethyl)acetanilide, in which the weight ratio of said methylurea compound to said chloroacetanilide is 1:1 to 1:3, dissolved in a solvent system comprising (i) 100 to 60% by weight of at least one material selected from the group consisting of an aromatic hydrocarbon solvent, liquid aromatic halocarbon solvent and a liquid aliphatic halocarbon solvent and (ii) 0 to 40% by weight of a cosolvent; said aromatic hydrocarbon solvent having a distillation point in the range between about 132° and 371° C. at atmospheric pressure and a flash point above 26° C., comprising more than 80% by weight of aromatics selected from alkylated benzenes and alkylated naphthalenes; said aromatic halocarbon being selected from monochlorobenzene, o-dichlorobenzene, trichlorobenzene and bromobenzene; and said liquid aliphatic halocarbon being one containing from one to three carbon atoms, at least one hydrogen atom and two or more halogen atoms per molecule; said concentrate having a greater amount of said methylurea dissolved in said solvent system than would dissolve therein in the absence of said chloroacetanilide.

2. The solution concentrate of claim 1 wherein the concentration of said mixture is 25–45% by weight.

3. The solution concentrate of claim 1 wherein the chloroacetanilide is 2-chloro-N-isopropylacetanilide.

4. The solution concentrate of claim 3 wherein the concentration of said mixture is 25–45% by weight.

5. The solution concentrate of claim 1 wherein the chloroacetanilide is 2-chloro-2',6'-diethyl-N-(methoxymethyl)acetanilide.

6. The solution concentrate of claim 5 wherein said solvent system comprises a mixture of said aromatic hydrocarbon and isophorone.

7. The solution concentrate of claim 6 wherein the concentration of said mixture is 25–45% by weight.

8. The solution concentrate of claim 1 also containing an effective amount of an emulsifying agent.

9. The solution concentrate of claim 8 in which said mixture is present in an amount of from 15–50% by weight, said emulsifying agent is present in an amount of from 1–10% by weight and said solvent system is present in an amount of from 40 to 84% by weight.

10. A method for increasing the solubility of 1-(3,4-dichlorophenyl)-3-methoxy-3-methylurea in a solvent system which comprises combining said urea with a chloroacetanilide, selected from the group consisting of 2-chloro-N-isopropylacetanilide and 2-chloro-2',6'-diethyl-N-(methoxymethyl)-acetanilide, in which the weight ratio of said urea compound to said chloroacetanilide is 1:1 to 1:3, dissolved in a solvent system comprising (i) 100 to 60% by weight of at least one material selected from the group consisting of an aromatic hydrocarbon solvent, liquid aromatic halocarbon solvent and a liquid aliphatic halocarbon solvent and (ii) 0 to 40% by weight of cosolvent; the resulting solution concentrate comprising from 15–50% by weight of said mixture of said urea and said chloroacetanilide; said aromatic hydrocarbon solvent having a distillation point in the range between 132° and 371° C. at atmospheric pressure and having a flash point above 26° C., comprising more than 80% by weight of aromatics selected from alkylated benzenes and alkylated naphthalenes; said aromatic halocarbon being selected from monochlorobenzene, o-dichlorobenzene, trichlorobenzene and bromobenzene; and said liquid aliphatic halocarbon being one of those containing from 1 to 3 carbon atoms at least one hydrogen atom and two or more halogen atoms per molecule; whereby a solution concentrate is formed having a greater amount of said urea compound dissolved in said solvent system than would dissolve therein in the absence of said chloroacetanilide.

11. The method of claim 10 wherein the concentration of said mixture is 25–45% by weight.

12. The method of claim 10 wherein said chloroacetanilide is 2-chloro-N-isopropylacetanilide.

13. The method of claim 12 wherein the concentration of said mixture is 25–45% by weight.

14. The method of claim 10 wherein said chloroacetanilide is 2-chloro-2',6'-diethyl-N-(methoxymethyl)acetanilide.

15. The method of claim 14 wherein said solvent system comprises a mixture of said aromatic hydrocarbon and isophorone.

16. The method of claim 15 wherein the concentration of said mixture is 25–45% by weight.

17. The method of claim 10 further characterized in that the solution concentrate contains an effective amount of an emulsifying agent.

18. The method of claim 17 wherein said emulsifying agent is present in an amount of from 1–10% by weight and said solvent system is present in an amount of from 40–84% by weight.

* * * * *